(12) United States Patent
Suehira

(10) Patent No.: US 8,390,819 B2
(45) Date of Patent: Mar. 5, 2013

(54) OPTICAL COHERENCE TOMOGRAPHY METHOD AND OPTICAL COHERENCE TOMOGRAPHY APPARATUS THAT REMOVES A MIRROR IMAGE OF AN ADJACENT REGION TO THE MEASUREMENT REGION

(75) Inventor: Nobuhito Suehira, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 476 days.

(21) Appl. No.: 12/709,731

(22) Filed: Feb. 22, 2010

(65) Prior Publication Data

US 2010/0226554 A1 Sep. 9, 2010

(30) Foreign Application Priority Data

Mar. 6, 2009 (JP) ................................. 2009-053794

(51) Int. Cl.
*G01B 11/02* (2006.01)
(52) U.S. Cl. ........................................ 356/497; 356/479
(58) Field of Classification Search .................. 356/479, 356/497, 503, 504; 351/206
See application file for complete search history.

(56) References Cited

U.S. PATENT DOCUMENTS

| 6,377,349 B1 | 4/2002 | Fercher |
| 7,823,782 B2 | 11/2010 | Yatagai et al. |
| 8,204,300 B2 | 6/2012 | Sugita et al. |
| 2006/0171503 A1* | 8/2006 | O'Hara et al. .................. 378/21 |
| 2009/0079993 A1 | 3/2009 | Yatagai et al. |
| 2010/0166293 A1 | 7/2010 | Sugita et al. |
| 2011/0299034 A1* | 12/2011 | Walsh et al. .................. 351/206 |
| 2012/0218557 A1 | 8/2012 | Sugita et al. |

FOREIGN PATENT DOCUMENTS

| JP | 11-325849 | 11/1999 |
| JP | 2000-046729 A | 2/2000 |
| JP | 2006-201087 A | 8/2006 |
| JP | 2008-298767 A | 12/2008 |
| WO | 2007/060973 A1 | 5/2007 |
| WO | 2010/009450 A1 | 1/2010 |

OTHER PUBLICATIONS

Zhang et al., Removal of a mirror image and enhancement of the signal-to-noise ratio in Fourier-domain optical coherence tomography using an electro-optic phase modulator, Jan. 15, 2005, vol. 30, No. 2, OPTICS LETTERS, pp. 147-149.*
Wang, "In vivo full range complex Fourier domain optical coherence tomography" Applied Physics Letters, 90, 054103 (Jan. 30, 2007).
"Ultrahigh-resolution optical coherence tomography by broadband continuum generation from a photonic crystal fiber," Yimin Wang, et al., OPTICS LETTERS, vol. 28, No. 3, Feb. 1, 2003, pp. 182-184.

* cited by examiner

*Primary Examiner* — Tarifur Chowdhury
*Assistant Examiner* — Michael P Lapage
(74) *Attorney, Agent, or Firm* — Fitzpatrick, Cella, Harper & Scinto

(57) ABSTRACT

An optical coherence tomography method according to the present invention comprising the steps of dividing an object to be measured into a plurality of measurement regions adjacent to one another in a direction of irradiation of a measurement light, and acquiring a measurement image for every measurement region based on a wavelength spectrum of a coherent light and acquiring a tomographic image for every measurement region by removing a mirror image of a tomographic image of an adjacent region being adjacent to the measurement region of the measurement image from the measurement image.

25 Claims, 7 Drawing Sheets

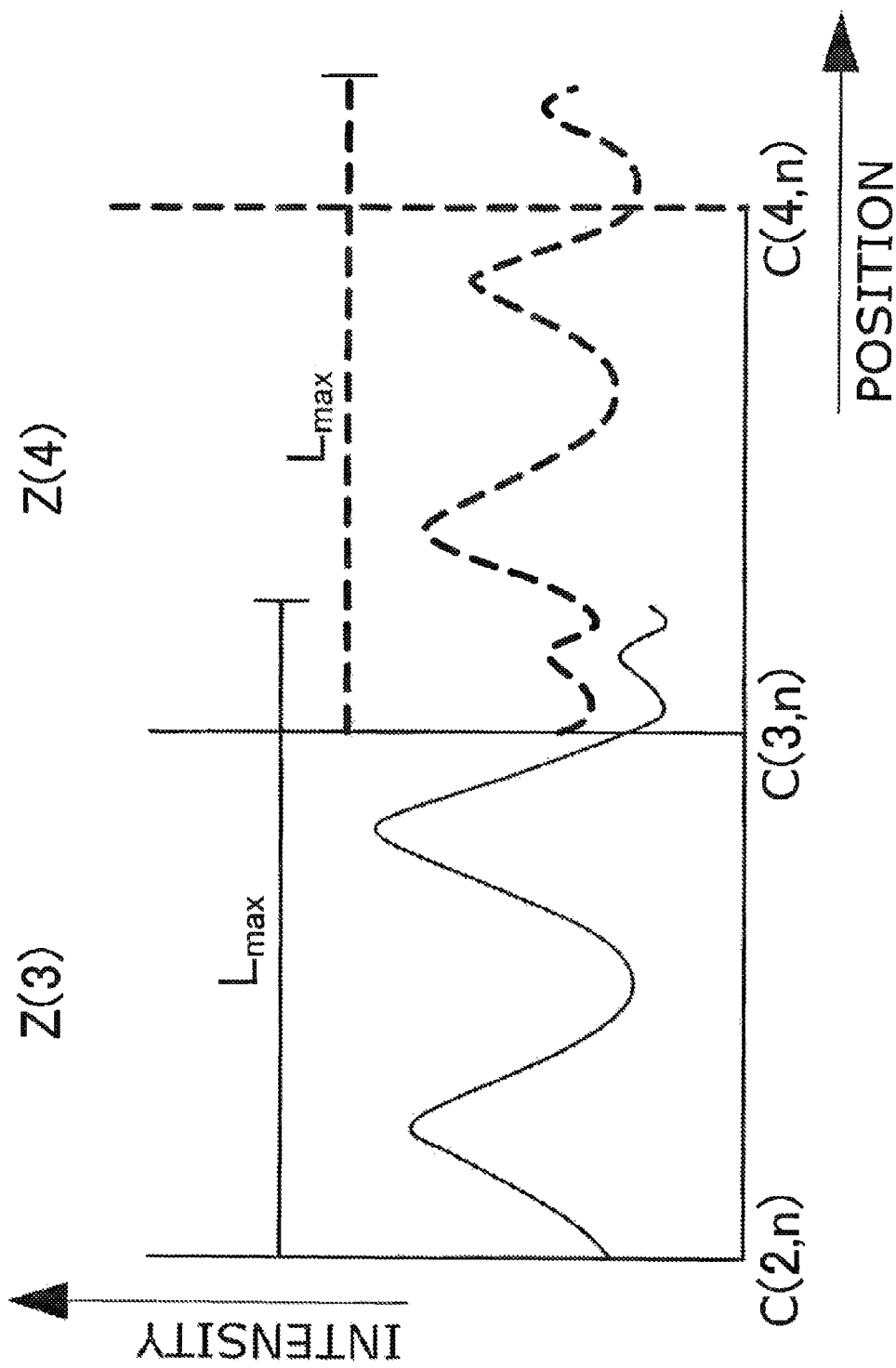

OPTICAL COHERENCE TOMOGRAPHY METHOD AND OPTICAL COHERENCE TOMOGRAPHY APPARATUS THAT REMOVES A MIRROR IMAGE OF AN ADJACENT REGION TO THE MEASUREMENT REGION

BACKGROUND OF THE INVENTION

1. Field of the Invention

The present invention relates to an optical coherence tomography method and an optical coherence tomography apparatus, and more particularly to an optical coherence tomography method and an optical coherence tomography apparatus, using a coherent optical system for use in the medical field.

2. Description of the Related Art

Currently, there are a wide variety of ophthalmic devices using optical devices. Examples of such ophthalmic devices include anterior eye imaging apparatuses, retinal cameras and scanning laser ophthalmoscopes (SLOs). Among them, optical coherence tomography (OCT) apparatuses can obtain tomographic images of objects to be measured at high resolution, and therefore are becoming indispensable devices for outpatient medical treatments specialized for retinas.

An OCT apparatus is disclosed, for example, in Japanese Patent Application Laid-Open No. H11-325849. In an OCT apparatus disclosed in Japanese Patent Application Laid-Open No. H11-325849, low coherent light is used. Light from a light source is divided into measurement light and reference light through a split optical path, such as a beam splitter. The measurement light is applied onto an object to be measured, such as a human eye, through a measurement optical path, and return light from the object to be measured is led to a detection position through a detection optical path. The return light as used herein refers to reflected light or scattered light that includes information on an interface of the object to be measured with respect to the irradiation direction of light. The reference light is led to a detection position through a reference optical path. Input to a detection position is coherent light resulting from interference between the return light and the reference light. Then, the wavelength spectrum of the coherent light is collectively acquired by the use of a spectrometer or the like, and the wavelength spectrum is Fourier transformed, thereby obtaining a tomographic image of the object to be measured. In general, an OCT apparatus that collectively measures the wavelength spectrum is termed a spectral-domain OCT (SD-OCT) apparatus.

With an SD-OCT apparatus, the depth of focus and a transversal resolution (the direction perpendicular to an irradiation direction of measurement light) can be adjusted by selecting a numerical aperture (NA) of a lens used for controlling a focusing position of the measurement light in an object to be measured. For example, the larger the numerical aperture is, the smaller the depth of focus is, but the higher the transversal resolution is. On the other hand, if the numerical aperture is reduced, the depth of focus becomes larger, but the transversal resolution becomes lower. In other words, the relationship between the depth of focus and the transversal resolution is a trade-off.

As a method that overcomes this relationship, dynamic focus OCT is disclosed in "OPTICS LETTERS Vol. 28, 2003, pp. 182-184". In this mode, time domain OCT (TD-OCT) that acquires a tomographic image while changing an optical path length is employed. Then, a tomographic image is acquired while changing the optical path length and moving the focus position of a lens in synchronization with each other. As a result, while the transversal resolution is maintained high, the measurement range of an object to be measured (the range in the irradiation direction of measurement light in an acquired tomographic image) can be increased.

SUMMARY OF THE INVENTION

In TD-OCT, however, measurement is performed while consecutively changing the optical path length. Therefore, it takes more time to acquire (measure) a tomographic image with TD-OCT than with SD-OCT. In order to achieve high-speed acquisition of a tomographic image having a large measurement range of an object to be measured and a high transversal resolution, a method of performing dynamic focusing in a spectral-domain mode is considered. As described above, in the spectral-domain mode, as the transversal resolution increases, the depth of focus decreases. Accordingly, to increase the measurement range, an object to be measured needs to be divided into a plurality of measurement regions adjacent to one another along the irradiation direction of measurement light for the purpose of measurement. As the result, a situation in which the coherence gate needs to be arranged in the interior of the object to be measured occurs. The term "coherence gate" refers to a position that is in the measurement optical path and that has the same optical distance as that of the reference optical path. This means that images that reflect each other are formed in adjacent regions across the coherence gate. The two images are equivalent, and therefore either of them may be employed for a tomographic image. Hereinafter, an image to be acquired (i.e., an image employed as the tomographic image in the region) is referred to as a "real image", and the other image is referred to as a "mirror image". In the case of adopting the SD-OCT mode, an image (measurement image) represented by coherent light includes a real image and a minor image, and therefore separating the real image from the mirror image is indispensable. In an apparatus disclosed in Japanese Patent Application Laid-Open No. 11-325849, in order to acquire a real image of one region, the position of the coherence gate needs to be changed a plurality of times and then measurement of a spectrum is performed. Therefore, it takes a long time for measurement.

Accordingly, an object of the invention is to provide an optical coherence tomography method and an optical coherence tomography apparatus, that can remove a mirror image from a measurement image by a simple method and can acquire a tomographic image in a short time.

An optical coherence tomography method that divides light from a light source into measurement light and reference light and acquires a tomographic image of an object to be measured based on a wavelength spectrum of coherent light of the reference light and return light, the return light returning from the object to be measured upon irradiating the measurement light onto the object to be measured, according to the present invention, the optical coherence tomography method comprising the steps of:

dividing the object to be measured into a plurality of measurement regions adjacent to one another in a direction of irradiation of the measurement light, and acquiring a measurement image for every measurement region based on the wavelength spectrum of the coherent light; and acquiring a tomographic image for every measurement region by removing a mirror image of the tomographic image of an adjacent region being adjacent to the measurement region of the measurement image from the measurement image.

An optical coherence tomography apparatus that divides light from a light source into measurement light and reference light and acquires a tomographic image of an object to be measured based on a wavelength spectrum of coherent light of the reference light and return light, the return light returning from the object to be measured upon irradiating the measurement light onto the object to be measured, according to the present invention, the optical coherence tomography apparatus comprising:

a measurement image acquisition unit configured to, with the object to be measured divided into a plurality of measurement regions adjacent to one another in a direction of irradiation of the measurement light, acquire a measurement image for every measurement region based on the wavelength spectrum of the coherent light; and a tomographic image acquisition unit configured to acquire a tomographic image for every measurement region by removing a mirror image of the tomographic image of an adjacent region being adjacent to the measurement region of the measurement image from the measurement image.

According to some aspects of the invention, it is possible to provide an optical coherence tomography method and an optical coherence tomography apparatus, that can remove a mirror image from a measurement image by a simple method and can acquire a tomographic image in a short time.

Further features of the present invention will become apparent from the following description of exemplary embodiments with reference to the attached drawings.

BRIEF DESCRIPTION OF THE DRAWINGS

FIG. 7 illustrates a method of image adjustments of real images.

DESCRIPTION OF THE EMBODIMENT

An optical coherence tomography apparatus according to this embodiment will be described below.

The optical coherence tomography apparatus according to the embodiment divides light from a light source into measurement light and reference light through a split optical path. The measurement light is irradiated through a measurement optical path onto an object to be measured. Return light returning from the object to be measured upon irradiation of the measurement light is led through a detection optical path to a detection position. The focus position of the measurement light in the object to be measured (irradiation direction) can be controlled by a focus drive mechanism. The reference light is led through a reference optical path to a detection position. In the reference optical path, a mirror is disposed, and the position of the coherence gate can be adjusted by a mirror drive mechanism. Since the coherence gate and the focus position can be controlled in synchronization with each other, it is possible to divide the object to be measured into a plurality of measurement regions adjacent to one another along the irradiation direction and sequentially perform measurement for every region.

Light led to the detection position (coherent light of the return light and the reference light) is resolved into its wavelength spectrum and is analyzed. Thus, a tomographic image of the object to be measured is acquired. In this embodiment, a measurement image is acquired for every measurement region based on the wavelength spectrum of the coherent light. By removing from the measurement image a mirror image of a tomographic image in an adjacent region that is adjacent to the measurement region of the measurement image, a tomographic image (real image) for every measurement region is acquired. By combining (joining together) the real images of all the measurement regions, a homographic image having a large measurement range and a high transversal resolution (a desired tomographic image) can be acquired.

Figure 1A:
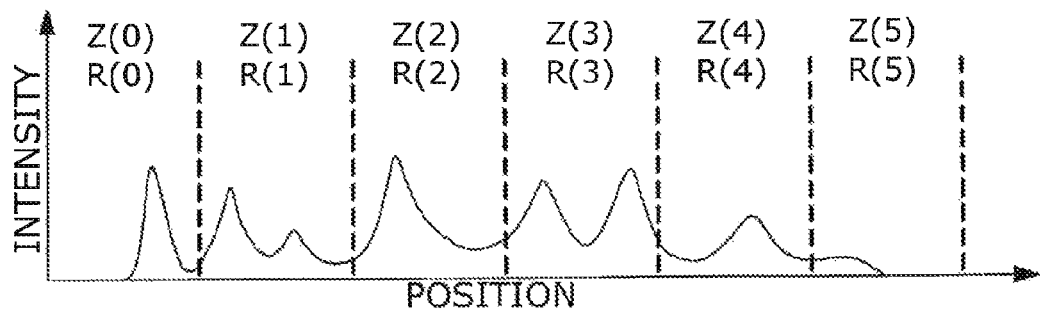
FIG. 1A illustrates an ideal tomographic image of an object to be measured.

Here, with reference to FIGS. 1A to 1D, the principle of a method of acquiring real images and a desired tomographic image with an optical coherence tomography apparatus according to this embodiment (an optical coherence tomography method according to this embodiment) is described. In FIGS. 1A to 1D, the vertical axis indicates the reflection intensity (intensity of light) and the horizontal axis indicates the position (in the irradiation direction) in the object to be measured. FIG. 1A illustrates an ideal tomographic image of an object to be measured. In the embodiment, the object to be measured is divided into measurement regions $Z(0)$ to $Z(5)$ at regular intervals, and measurement is performed on a region basis. Reference numerals $R(0)$ to $R(5)$ represent real images of the measurement regions $Z(0)$ to $Z(5)$, respectively. the embodiment, the measurement region $Z(0)$ is disposed as a first measurement region at an end of the object to be measured. A plurality of measurement regions are set so that first to xth measurement regions (x is an integer greater than 1; the measurement regions $Z(0)$ to $Z(5)$ in examples of FIGS. 1A to 1D) are arranged sequentially in a direction of irradiation of measurement light. Note that with an OCT apparatus, a portion having a large difference in refractive index is measured as a large signal. Accordingly, a region at the end of the object to be measured is a region adjacent to a range in which the difference in refractive index can be ignored. Note that even in the interior of the object to be measured, if the difference in refractive index can be ignored in a range equal to or greater than the width of the measurement region, the measurement region in question and a region disposed in the outside thereof can be regarded as different objects. Therefore, such a measurement region may be regarded as a region at the end of the object to be measured.

Figure 1B:
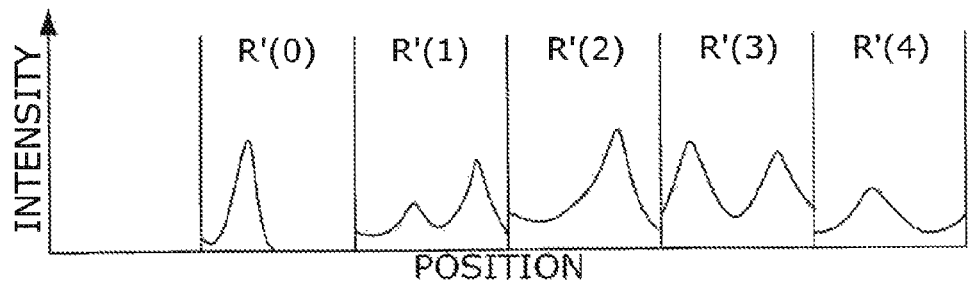
FIG. 1B illustrates mirror images reflected in measurement regions.

FIG. 1B schematically illustrates a mirror image reflected in the measurement region $Z(i)$ (a mirror image to be superimposed on a real image of the measurement region $Z(i)$) when the coherence gate is placed at the boundary of the measurement region $Z(i-1)$ and the measurement region $Z(i)$ ($i>1$). Since the mirror image reflected in the measurement region $Z(i)$ is a mirror image of the real image of the measurement region $Z(i-1)$, the mirror image is denoted by a reference character $R'(i-1)$. Note that a measurement region of $i=0$ (the measurement region $Z(0)$) is a region at the end of the object to be measured, and therefore no mirror image appears.

Figure 1C:
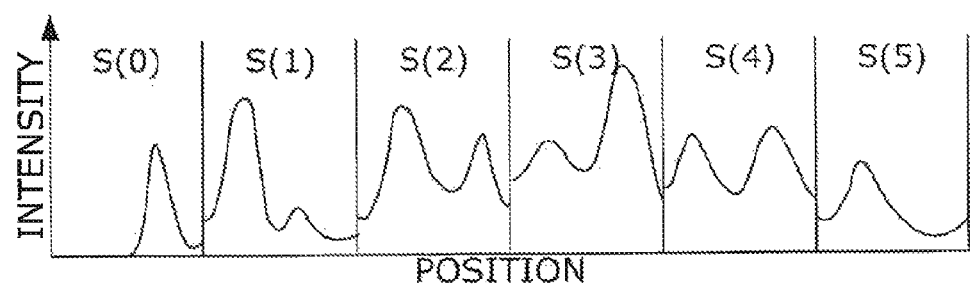
FIG. 1C illustrates a measurement image of each measurement region.

FIG. 1C illustrates measurement images S(0) to S(5) of measurement regions when the coherence gate is placed at the boundary between the measurement region Z(i−1) and the measurement region Z(i). The measurement images of the measurement regions Z(1) to Z(5) are images in each of which a mirror image is superimposed on a real image. However, as described above, no mirror image appears in the measurement region Z(0), and therefore the measurement image S(0) of the measurement region Z(0) is a real image. The measurement image S(i) is expressed by expressions 1-1 and 1-2.

$$S(i)=R(i)\ i=0 \quad (1\text{-}1)$$

$$S(i)=R(i)+R'(i-1)\ i=1\ \text{to}\ 5 \quad (1\text{-}2)$$

Expression 1-1 represents that the measurement image S(0) of the measurement region Z(0) is a real image R(0). Expression 1-2 represents that a real image R(i) of the measurement region Z(i) can be obtained by subtracting a mirror image R'(i−1) of a real image R(i−1) from the measurement image S(i) of the measurement region Z(i).

Given that the real image obtained by removing the mirror image from the measurement image is denoted by a reference character C(i), the real image C(i) is expressed by expressions 2-1 and 2-2 (reference character C'(i−1) denotes a mirror image of a real image C(i−1).

$$C(i)=S(i)\ i=0 \quad (2\text{-}1)$$

$$C(i)=S(i)-C'(i-1)\ i=1\ \text{to}\ 5 \quad (2\text{-}2)$$

Figure 1D:
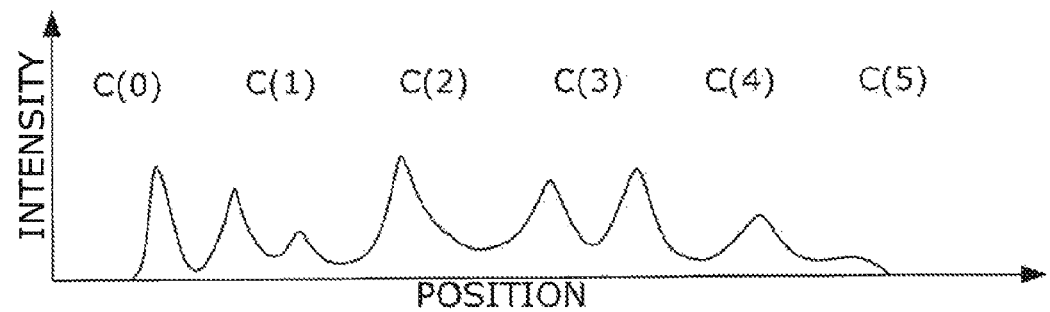
FIG. 1D illustrates a calculated real image of each measurement region.

The mirror image C'(i−1) can be calculated from the real image C(i−1). As described above, no mirror image appears in a first measurement region (the measurement region Z(0)). Therefore in the embodiment, the measurement image S(0) is employed as a tomographic image (real image) C(0) for the first measurement region. For the second to xth measurement regions in sequence, a Yth (2≦Y≦X) real image is obtained by removing a mirror image of a real image of a (Y−1)th measurement region from a measurement image of a Yth measurement region. That is, in an example of FIG. 1D, the real image C(i) is calculated sequentially for i=1 to 5. This allows a real image to be acquired for every measurement region. By joining together acquired real images, a desired tomographic image can be obtained (FIG. 1D).

Note that in the embodiment, the real image C(i) is calculated sequentially from i=1; however, the calculation method is not limited to that in the embodiment. For example, in cases where the measurement region Z(5) is disposed at the end of the object to be measured and the coherence gate is placed at the boundary between the measurement region Z(I +1) and the measurement region Z(I) (I is not less than 0 and not more than y, and y =4 in examples of FIGS. 1A to 1D), and the measurement region Z(5) may be the first measurement region. More specifically, in such a case, the measurement image S(5) becomes a real image C(5), the minor image of the real image C(I +1) of the measurement region Z(I +1) is reflected in the measurement region Z(I). Therefore, the real image C(I) can be obtained by subtracting a mirror image C(I +1) from the measurement image S(I). A real image of each measurement region can be obtained by calculating the real image C(I) sequentially for I =4 to 0.

It is conceivable that the ends are positioned in the interior of the object to be measured. For example, it is conceivable that the measurement region Z(2) and the measurement region Z(4) are regions at the ends of the object to be measured, and there is no structure in the measurement region Z(3). In this case, if the coherence gate is placed at the boundary between the measurement region Z(i−1) and the measurement region Z(i) the measurement image S(3) becomes the mirror image of the real image C(2), and the measurement image S(4) becomes the real image C(4). Therefore, in such a case, real images of the measurement regions Z(0), Z(1) and Z(5) may be calculated in the same way as described above.

In this way, with an optical coherence tomography apparatus according to this embodiment, measurement of each measurement region is performed at least once, and using its data, a real image of each measurement region is calculated. More specifically, with a simple method of removing a mirror image of a measurement image by the use of a real image of another region, a tomographic image can be obtained in a short time. Further, by joining together obtained real images (tomographic images); a tomographic image having a large measurement range in the object to be measured and a high transversal resolution can be obtained at high speed. Thus, a high-speed, dynamic-focus OCT apparatus can be implemented.

EXAMPLE 1

Next, a specific example of the optical coherence tomography apparatus according to this embodiment is described. Specifically, an ophthalmic OCT apparatus to which this invention is applied is described below.

<Configuration of Optical Apparatus>

Figure 2:
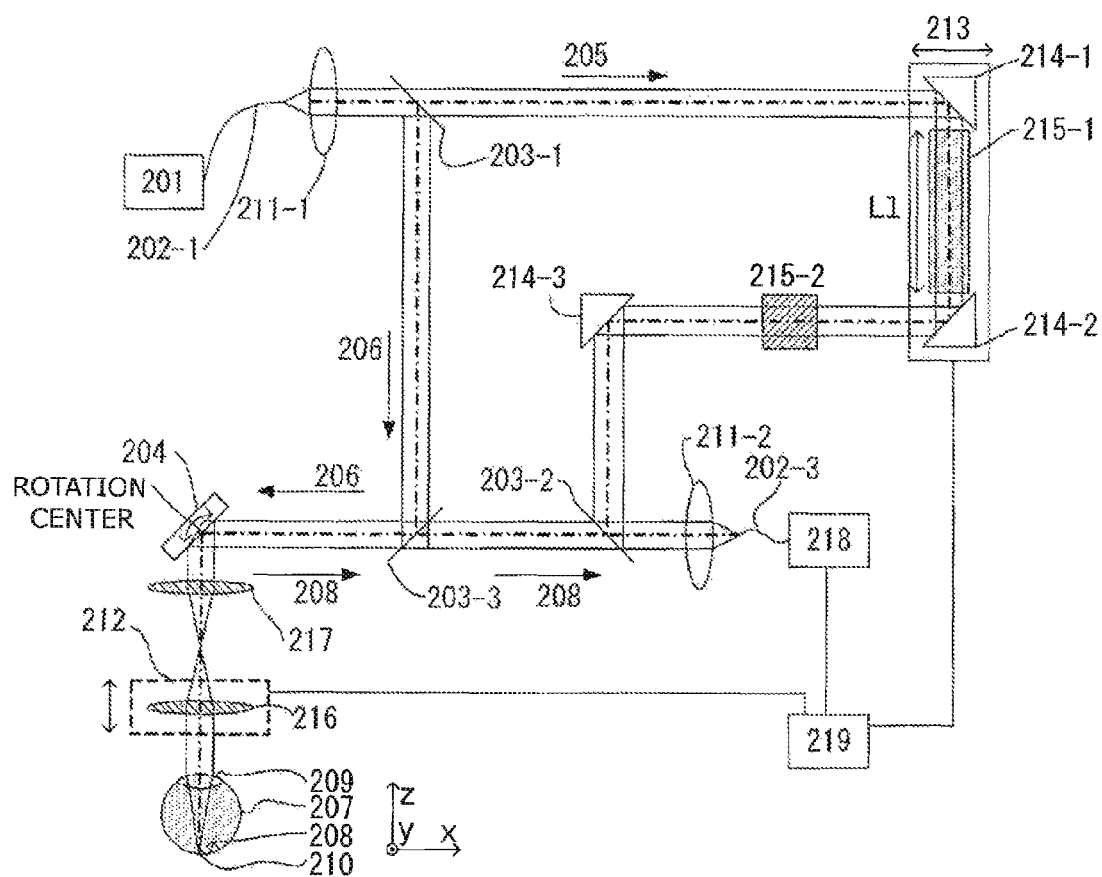
FIG. 2 illustrates a configuration of a Mach-Zehnder interference system used in an OCT apparatus according to the example 1.

FIG. 2 illustrates a configuration of a Mach-Zehnder interference system used in an OCT apparatus according to this example. Light emitted from a light source 201 (emitted light) passes through a single mode fiber 202-1 and is led to a lens 211-1. The emitted light is divided into reference light 205 and measurement light 206 by a beam splitter 203-1. After an eye 207, or an object to be measured, is irradiated with the measurement light 206, the measurement light 206 returns as return light 208, which is caused by reflection or scattering. The reference light and the return light pass through a beam splitter 203-2, a lens 211-2 and a single mode fiber 202-3 and are incident on a spectrometer 218. Data such as a wavelength spectrum of light (coherent light of the return light and the reference light) acquired in the spectrometer 218 is input to a computer 219. Note that the light source 201 is a super luminescent diode (SLD), which is a representative, low-coherent light source. Considering the fact that the object to be measured is an eye, it is preferable that the emitted light be infrared light (e.g., light having a center wavelength of 840 nm and a bandwidth of 50 nm).

A description is given of the reference optical path of the reference light 205. The reference light 205 resulting from division by the beam splitter 203-1 is sequentially incident on mirrors 214-1 to 214-3. The reference light 205 is led to the beam splitter 203-2 and is incident on the spectrometer 218. Note that the reference light 205 passes through the interior of a dispersion-compensating glass 215-1 between the minors 214-1 and 214-2. The length of the dispersion-compensating glass 215-1 is L1, which is preferably equal to twice the depth of a typical eye. This length is preferred so as to compensate the reference light 205 for dispersion caused when the measurement light 206 reflects and scatters in the eye 207. In this example, the length L1 is given to be 46 mm. This length is twice 23 mm regarded as the average diameter of an eyeball of Japanese people. Further, the minors 214-1 and 214-2 can be moved in directions indicated by arrows in FIG. 2 by a minor drive mechanism 213. By moving the positions of the minors 214-1 and 214-2, the optical path length of the reference light 205 can be adjusted and controlled. The reference light 205 passes through the interior of a dispersion-compensating glass 215-2 between the minors 214-2 and 214-3. The dispersion-compensating glass 215-2 is used for dispersion compensating of an objective lens 216 and a scan lens 217 used for scanning an eye.

A description is given of the measurement optical path of the measurement light 206. The measurement light 206 resulting from division by the beam splitter 203-1 is reflected from a beam splitter 203-3 and is incident on a mirror of an XY scanner 204. The XY scanner 204 performs a raster scan of a retina 210 in a direction perpendicular to the optical axis (irradiation direction). The center of the measurement light 206 is adjusted so as to be in alignment with the center of rotation of a mirror of the XY scanner 204. The objective lens 216 and the scan lens 217 constitute an optical system for scanning the retina 210 (leading the measurement light to various positions of the retina), and are used for scanning the retina 210 with a point in the vicinity of a cornea 209 used as a supporting point. In this example, focal distances of the objective lens 216 and the scan lens 217 are 50 mm and 50 mm, respectively. The focus position of the objective lens 216 (in the irradiation direction) can be adjusted by a focus drive mechanism 212. When the measurement light 206 is incident on the eye 207, the measurement light 206 reflects and scatters by the retina 210, and returns as the return light 208. The return light 208 passes through the same optical path up to the beam splitter 203-3 as the measurement light 206, and passes through the beam splitter 203-3. Then the return light 208 is led by the beam splitter 203-2 to be incident on the spectrometer 218.

Note that the focus drive mechanism, the minor drive mechanism, the XY scanner 204 and the spectrometer 218 are controlled by the computer 219 to perform desired operation. The computer 219 performs data processing, data saving and image processing of the spectrometer 218.

<Measurement Range>

Figure 3:
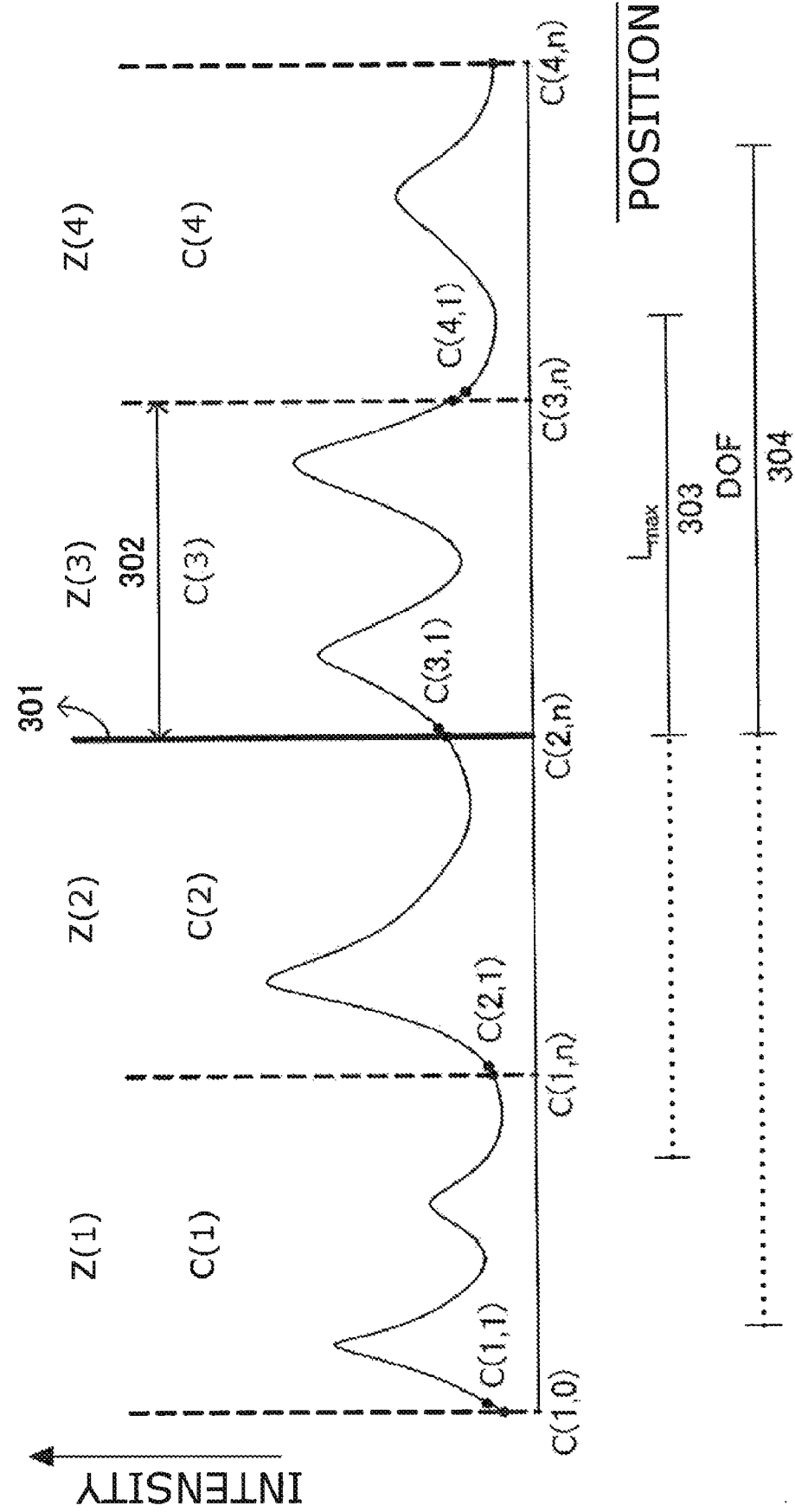
FIG. 3 illustrates widths of measurement regions.
Figure 4:
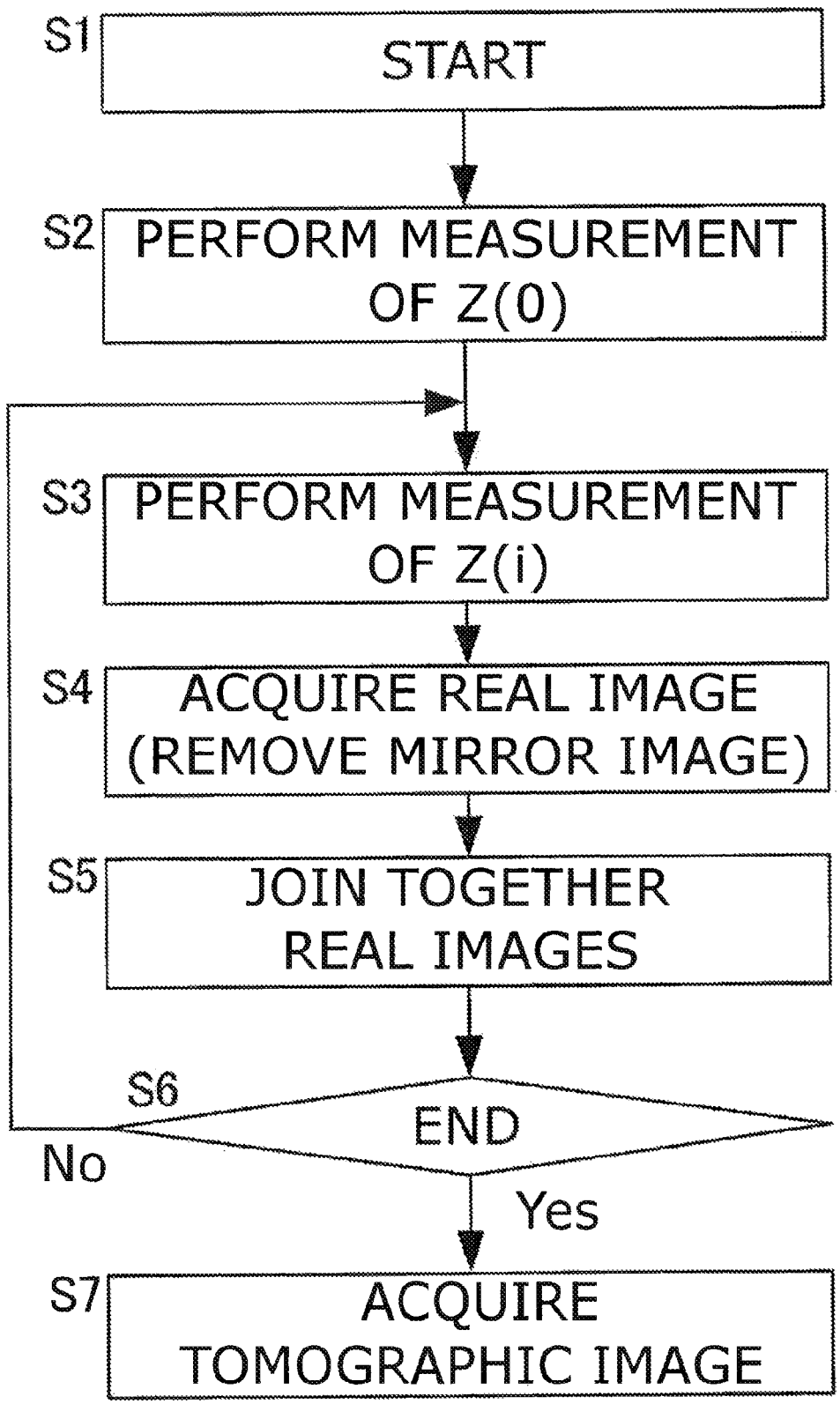
FIG. 4 is a flow chart illustrating a method of analyzing measurement image data in the example 1.

Next, with reference to FIG. 3, the width (in the irradiation direction) of the measurement region is described. In FIG. 3, the vertical axis indicates the reflected intensity and the horizontal axis indicates the position (in the light application direction) in the interior of an object to be measured. FIG. 3 schematically illustrates a case where a coherence gate 301 is placed between the measurement region Z(3) and the measurement region Z(2) adjacent thereto and measurement of measurement region Z(3) is performed. Reference numeral 302 denotes a width of each measurement region, reference character 303 denotes the measurement depth, and reference character 304 denotes the depth of focus. The measurement depth and the depth of focus will be described below.

The depth of focus (DOF) represents the visible range of an obtained image. The depth of focus is expressed by expression 3 (optical distance) using the numerical aperture (NA) of a lens used for focusing measurement light into an object to be measured and a center wavelength λ of a light source. In FIG. 3, the plus side of the range obtained by expression 3 is indicated by continuous lines and the minus side is indicated by broken lines.

$$DOF = \pm \lambda/(2NA^2) \tag{3}$$

In cases where an object to be measured is an eye and the object to be measured is divided into six measurement regions, if the width of each measurement region is 500 μm, it is preferable that the depth of focus be longer than the total length of 1000 μm (±500 μm). Note that in a typical SD-OCT apparatus, the whole length of the depth of focus is about 3 mm. As a matter of course, if the number of division increases, the measurement region can be made smaller and therefore the depth of focus can also be decreased. Note that a region exceeding the depth of focus to some extent is not without the possibility of measurement. The focus need not be set at the position of the coherence gate. However, in order to obtain a uniform image, it is preferable that the depth of focus be larger than the width of each measurement region. In the case of an OCT apparatus, the NA can be changed by changing the diameter of a light beam. In general, if the diameter of a light beam incident on an eye increases, the NA increases.

The measurement depth represents a range in which aliasing does not occur (occurrence of aliasing makes measurement difficult). The measurement depth is expressed by expression 4 (optical distance) using the number N of pixels (even number, typically the powers of 2, such as 1024 and 2048) of a line sensor of a spectrometer and a spectral bandwidth ΔK of the wave number detected by the spectrometer. In FIG. 3, the plus side and the minus side of the range obtained by expression 4 are indicated by continuous lines and broken lines, respectively.

$$L\max = \pm N/(4\Delta K) \tag{4}$$

Assuming that the center wavelength of measurement light is 840 nm, the bandwidth is 50 nm and the number of pixels of the line sensor of the spectrometer is 1024, the range that can be measured extends up to an optical distance of about ±3.4 mm. Note that the measurement depth represented by expression 4 is a theoretical value, and in fact an actual number of sampling times is less than N because of the optical resonation of a spectrometer. The range that can be accurately replaced (measured) is therefore smaller than the theoretical measurement depth. Accordingly, the width of a measurement region needs to be set to be less than the theoretical measurement depth. In general, the relationship of the width of the measurement region<the theoretical measurement depth is satisfied. Further, in order to obtain a uniform image, it is preferable that the depth of focus (whole length) and the width of a measurement region satisfy the relationship of expression 5. That is, it is preferable that the width of the measurement region be less than one half of the depth of focus when a measurement image of the measurement region in question is acquired.

$$2 \times \text{the width of the measurement region} < \text{the depth of focus (whole length)} \tag{5}$$

In discrete Fourier transformation, each element constituting a measurement image has a discrete value which is given by expression 6 (optical distance). Here t is an integer for $0 \leq t \leq N/2$.

$$L = t/(2\Delta K) \tag{6}$$

Numerical depth resolution δ(L) is expressed by expression 7. The numerical depth resolution δ(L) is also an interval per pixel. In this example, the numerical depth resolution δ(L) is an optical distance of about 6.8 μm.

$$L\min = \delta(L) = 1/(2\Delta K) \tag{7}$$

<Signal Processing>

With reference to FIGS. 1A to 1D and FIG. 4, a method of analyzing data of measurement images (measurement image data) is described. In this example, a case in which the coherence gate is placed at the boundary between the measurement region Z(i−1) and the measurement region Z(i), and measurement of the measurement region Z(i) is performed is described. Hereinafter, measurement image data of the measurement region Z(i) is denoted by reference character S(i, k). In this denotation, i is a region number from 0 to M−1, and k is an element number from 0 to n in the region (both i and n are integers). M is the number of regions, and n is the number of elements that satisfy n<N/2. N is the number of pixels of the line sensor. If the width of a measurement region is about 500 μm (because δ(L)=6.8 μm in this example), n=500/6.8=about 74 pixels. The width of the measurement region can be decreased by increasing the number of divisions, and therefore n is decreased with respect to the number of pixels of the line sensor. Note that it is assumed that the position of measurement image data S(i−1, n) is identical to the position of measurement image data S(i, 0), and the coherence gate is placed at this position. Similarly, data of a real image of each measurement region (real image data) is denoted by reference character C(i, k).

In step S1, measurement starts. Note that the initial value of i is taken to be 0.

In step S2, the measurement image data of the measurement region Z(i) (i.e., Z(0)) is acquired (a measurement image acquisition unit). Because the object to be measured is an eye, the coherence gate is placed at a position on the side of a cornea with respect to a retina. After the coherence gate is placed on the cornea side, the measurement image begins to change as the coherence gate is moved toward the retina. More specifically, the measurement image approaches closer to the coherence gate in synchronization with the movement of the coherence gate. As a result of movement, when the measurement image reaches a desired position, measurement of the measurement region Z(0) is performed. The desired position refers to a region where no mirror image is produced. Note that the focus position is moved in synchronization with the position of a mirror. Since no mirror image is produced in the measurement region Z(0), a real image C(0, k) can be directly acquired ram a measurement image S(i, k) as expressed by expression 8. Then one is added to i, and the procedure proceeds to step S3.

$$C(0, k) = S(0, k) \quad 0 \leq k \leq n \quad (8)$$

In step S3, the coherence gate is placed at the boundary between the measurement region Z(i−1) and the measurement region Z(i), and measurement of the measurement region Z(i) is performed. More specifically, measurement image data S(i, k) of the measurement region Z(i) is acquired (a measurement image acquisition unit). Note that measurement image data S(0, 0) is not tomographic data (there is no structure of the object to be measured at the position of the element), and therefore measurement image data S(0, 1) may be used in place of the measurement image data S(0, 0).

In step S4, mirror image data is removed from the measurement image data S(i, k) acquired in step S3 to acquire real image data C(i, k) (a tomographic image acquisition unit). The removed mirror image data is acquired by reversing relative to the position of the coherence gate (in this example, the boundary between the measurement region and the adjacent region that is adjacent to the measurement region). More specifically, real image data C(i−1, n−k) as the mirror image data is removed from the measurement image data S(i, k). Note that real image data C(i, 0) is data at the position where the coherence gate is placed, and therefore is equal to real image data C(i−1, n) (expression 9-1). The calculated real image data C(i, k) is expressed by expression 9-2.

$$C(i, 0) = C(i−1, n) \quad k=0 \quad (9-1)$$

$$C(i, k) = S(i, k) − C(i−1, n−k) \quad 0 < k \leq n \quad (9-2)$$

In step S5, the real image data C(i, k) acquired for every measurement region is joined together. If i is smaller than a desired value (5 in examples of FIGS. 1A to 1D) (in this case, measurement continues; Yes in step S6), one is added to i, and the procedure returns to step S3. If i reaches the desired value (i=5; in this case, measurement ends; No in step S6), the procedure proceeds to step S7 and then the procedure ends. By joining together real image data of all the regions, the desired tomographic image is obtained.

It should be noted that calculation is made with the coherence gate placed at the boundary of the measurement regions in this example; however, an error due to the spectrum of a light source is sometimes mixed to a component of S(i, k) with i in a lower order. In such a case, when a measurement image is acquired, the position of the coherence gate may be set on a side of the adjacent region with respect to the boundary between the measurement region and the adjacent region. For example, when measurement of the measurement region Z(i) is performed, the coherence gate should be shifted from the boundary between the measurement region Z(i−1) and the measurement region Z(i) toward the measurement region Z(i−1) by several to several tens of elements. The number of shifted elements may be determined depending on the coherence function of a light source, or the like.

In this example, whenever a real image is acquired, the real image is joined to other real images. All real images may be joined together after they have been acquired. Real images may be calculated after all measurement images have been acquired. As a matter of course, if the structure of an object to be examined is unclear, a process of searching a measurement region in which no mirror image is produced may be inserted. The measurement region in which no mirror image is produced is a portion where the coherence gate is moved and a measurement image is moved only in one direction.

EXAMPLE 2

Figure 5:
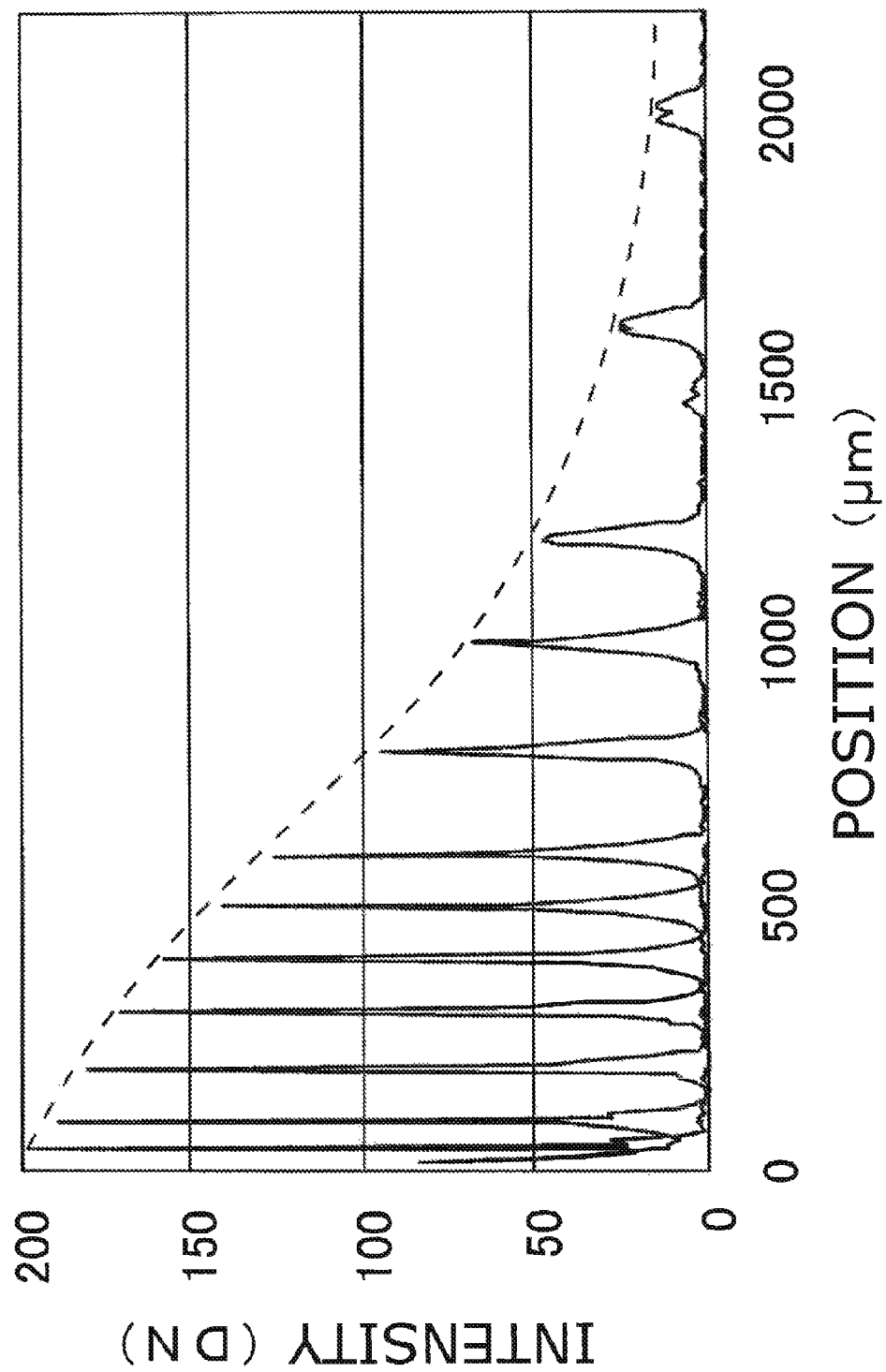
FIG. 5 illustrates a relationship of a distance between the coherence gate and a mirror and a measured intensity when the mirror is used as an object to be measured.

In example 2, a method of solving a problem due to a phenomenon specific to the SD-OCT is described. With reference to FIG. 5, the phenomenon specific to the SD-OCT is described. FIG. 3 illustrates a relationship of a distance between a coherence gate and a mirror for horizontal axis and a measured intensity for vertical axis (reflected intensity) in the case of using the mirror as an object to be measured. Specifically, reflected intensities (digital values) measured when the position of the mirror is distant from the coherence gate by 50, 100, 150, 200, 300, 400, 500, 600, 800, 1000, 1200, 1600 and 2000 μm are shown. The dotted line schematically shows the envelop of their results (changes in intensity with respect to the position in the irradiation direction in the measurement region), which is a so-called attenuation function. In FIG. 5, as the position of the mirror more distant from the coherence gate, the intensity attenuates more. This is called "roll-off" or the like, and occurs because of the resolution of a spectrometer and so on.

As described above, in the case of the phenomenon occurring, the intensity is stronger as the position is closer to the coherence gate whereas the intensity is weaker as the position is more distant from the coherence gate. Therefore, at a boundary of measurement regions, the intensity is strong in one region whereas the intensity is weak in the other region. This causes a lump in measured intensity between regions adjacent to each other.

<Signal Processing>

Figure 6:
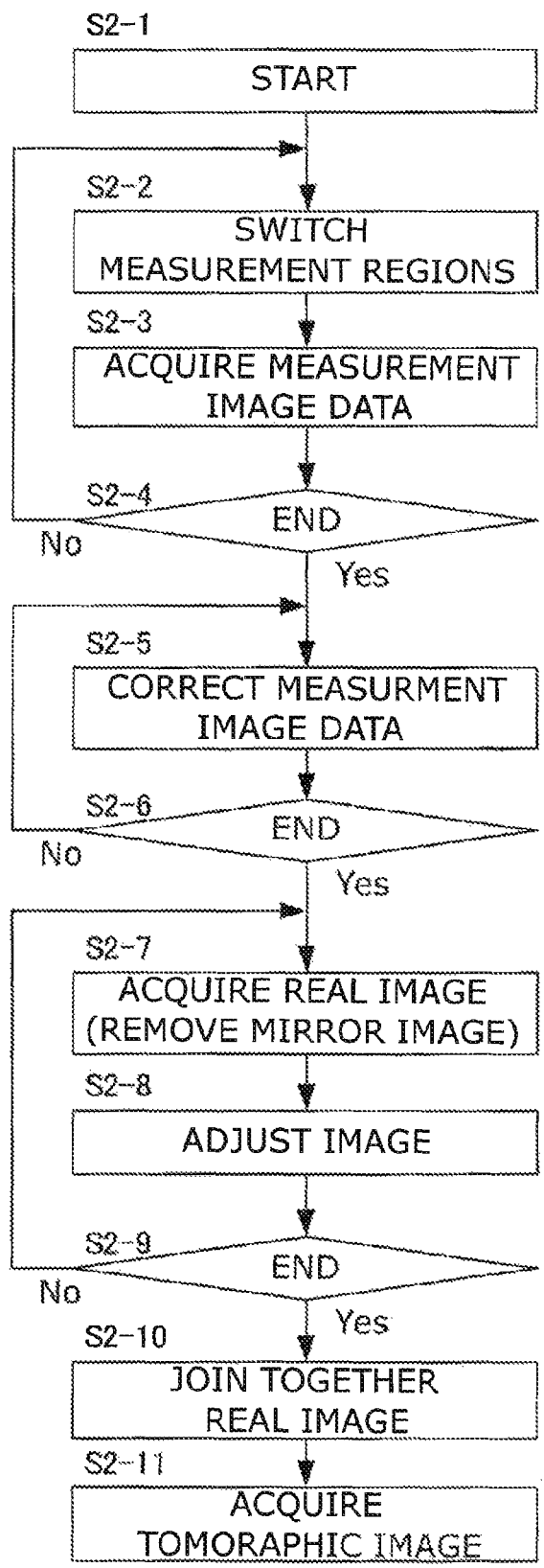
FIG. 6 is a flow chart illustrating a method of analyzing measurement image data in the example 2.

With reference to FIG. 6, a method of signal processing (a method of analyzing measurement image data) when such a phenomenon occurs is described.

In step S2-1, measurement starts.

In steps S2-2 to S2-4, measurement image data is sequentially acquired while measurement regions are switched. Note that in this example, a measurement image is acquired in a range (e.g., $0 \leq k \leq N-1$) broader than the width (e.g., 500 μm ($0 \leq k \leq n$)) of a measurement region.

In steps S2-5 and S2-6, measurement image data of each measurement region is sequentially corrected according to a correction function based on the above-mentioned attenuation function. More specifically, an optical coherence tomography apparatus stores in advance or acquires the above-mentioned correction function, and performs correction for every measurement position (element position) using a value of correction function corresponding to the position (a value obtained by substituting the position for the correction function; correction data). Given that data used for correction is correction data $D(i, k)$, the corrected measurement image data (correction image data) $H(i, k)$ is expressed by expression 10.

$$H(i, k) = S(i, k)/D(i, k) \qquad (10)$$

Note that the correction function may be an attenuation function itself obtained from a theory or an experiment, may also be an approximate function (a straight line or a secondary curve) or the attenuation function, and nay also be a sum or a product of the attenuation function and a given coefficient. Any function may be used if it can eliminate a phenomenon as described above.

The subsequent processing is the same as in example 1. More specifically, the corrected measurement image data $H(i, k)$ is used in place of the measurement image data $S(i, k)$.

Note that a single correction function may be used; however, if characteristics (the above-mentioned characteristics; the attenuation function) differ from one measurement region to another, a correction function according to every measurement region is preferably prepared (it is preferable that a correction function that differs for every measurement region). For example, in cases where the depth of focus varies depending on the position of the focus, the characteristics vary for every measurement region, and therefore such preparation is effective.

In steps S2-1 to S2-9, a mirror image is removed from a measurement image to acquire a real image for every measurement region and an image adjustment of the real image is performed for every measurement region. The image adjustment is adjustment of the pixel value of a real image and the position of a measurement region (the position in a direction of irradiation of measurement light). For example, in example 1, the position of the real image data $C(i, 0)$ and the position of the real image data $C(i-1, n)$ are identical to each other. However, their positions are sometimes displaced from each other. This is due to a position error of the coherence gate, an intensity error of a light source, and the like.

With reference to FIG. 7, the image adjustment is described. In FIG. 7, the vertical axis indicates the reflected intensity, and the horizontal axis indicates the position (in the irradiation direction) in the object to be measured. In FIG. 7, real images of the measurement regions $Z(3)$ and $Z(4)$ adjacent to each other are indicated by a continuous line and a broken line, respectively. A real image of the measurement region $Z(i)$ overlaps a real image of the measurement region $Z(i+1)$ in the range of $k > n$. Part or all of data of the overlapping portion is used for the image adjustment. Interpolation is performed between real image data obtained in the range of $k > n$, and data obtained by the interpolation may be used. Ideally, the real image data is adjusted so that the overlapping portions match each other. Note that assuming that the real image of the measurement region $Z(3)$ has already been adjusted, adjusting the real image of the measurement region $Z(4)$ so as to match the real image of the measurement region $Z(3)$ is described below.

An adjustment of the positions of the measurement regions (i.e., an adjustment in the horizontal axis direction of FIG. 7) is performed so that the intensity difference of the overlapping portion of tomographic images (the continuous line and the broken line) of the measurement region and its adjacent region is fixed. That is, in order to cause the intensity difference of the overlapping portion of the continuous line and the broken line to be fixed (e.g., to minimize the dispersion of intensity differences of the overlapping portion), the broken line is shifted in the horizontal axis direction. If in the overlapping portions, there is a specific peak in each of the real images, adjustment may be performed so that their peak positions match each other. Intensity adjustment (i.e., an adjustment in the vertical axis direction of FIG. 7) is performed so that the intensity difference of the overlapping portion of tomographic images (the continuous line and the broken line) of the measurement region and its adjacent region is minimum. That is, in order to cause the intensity difference of the overlapping portion of the continuous line and the broken line to be minimum (e.g., to make the total of absolute values of intensity differences of the overlapping portion minimum), the broken line is shifted in the vertical axis direction. Note that in the image adjustment, only one of the position and the intensity of the measurement region may be adjusted. If both the position and the intensity of the measurement region are adjusted, it is preferable that the intensity be adjusted after the position is adjusted.

In step S2-10, real images acquired for all the measurement regions are joined together. Thus, in step S2-11, the desired tomographic image can be acquired. Note that when the real images are joined together, for the overlapping portions, their average values may be used, and an element whose number is greater than n may be ignored.

As a result, data for every measurement region can be smoothly connected. This enables a more accurate tomographic image to be obtained.

As described above, according to an optical coherence tomography apparatus of the present embodiment, a mirror image is produced from a tomographic image (real image) in the adjacent region (adjacent to a measurement target region). The acquired mirror image is removed from a measurement image of the measurement target region. With such a simple method, a mirror image can be removed from a measurement image. Thus, a tomographic image (real image) can be acquired in a short time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-053794, filed on Mar. 6, 2009, which is hereby incorporated by reference herein in its entirety.

What is claimed is:

1. An optical coherence tomography method that divides light from a light source into measurement light and reference light and acquires a tomographic image of an object based on a wavelength spectrum of interfering light of the reference light and return light, the return light returning from the object upon irradiating the measurement light onto the object, the optical coherence tomography method comprising the steps of:

acquiring a measurement image based on the wavelength spectrum at each of a plurality of measurement regions of the object adjacent to one another in a direction of irradiation of the measurement light; and acquiring a tomographic image at each of the plurality of measurement regions by removing a mirror image of a tomographic image of an adjacent region being adjacent to the measurement region from the measurement image.

2. The optical coherence tomography method according to claim 1, wherein in the step of acquiring the measurement image, the plurality of measurement regions are set so that a first measurement region is disposed at an end of the object, and first to Xth (X is an integer greater than one) measurement regions are arranged sequentially in the direction of irradiation of the measurement light, and wherein in the step of acquiring the tomographic image for every measurement region, for the first measurement region, the measurement image is employed as the tomographic image, and for the second to Xth measurement regions, in turn, the tomographic image of a Yth ($2 \leqq Y \leqq X$) measurement region is acquired by removing the mirror image of the tomographic image of a (Y−1)th measurement region from the measurement image of the Yth measurement region.

3. The optical coherence tomography method according to claim 1, wherein a width of the measurement region in the direction of irradiation is smaller than one half of a depth of focus upon acquiring the measurement image of the measurement region.

4. The optical coherence tomography method according to claim 1, further comprising a step of correcting the measurement image according to a correction function determined based on an attenuation function representing a change in intensity with respect to a position in the measurement region in the direction of irradiation, wherein, in acquiring the tomographic image for every measurement region, the tomographic image for every measurement region is acquired by removing the mirror image of the tomographic image of the adjacent region from the corrected measurement image.

5. The optical coherence tomography method according to claim 4, wherein the correction function differs for every measurement region.

6. The optical coherence tomography method according to claim 1, further comprising a step of adjusting, for every measurement region, an intensity of the tomographic image and/or a position of the measurement region in the direction of irradiation.

7. The optical coherence tomography method according to claim 6, wherein the measurement image is acquired in a range larger than the measurement region, and wherein when the position of the measurement region in the direction of irradiation is adjusted for every measurement region, the position is adjusted so that a difference in intensity of an overlapping portion of the tomographic images of the measurement region and an adjacent region thereto is fixed.

8. The optical coherence tomography method according to claim 6, wherein the measurement image is acquired in a range larger than the measurement region of the measurement image, and wherein when the intensity of the tomographic image is adjusted for every measurement region, the intensity is adjusted so that a difference in intensity of an overlapping portion of the tomographic images of the measurement region and the adjacent region is minimum.

9. The optical coherence tomography method according to claim 1, wherein the adjacent region is adjacent to the measurement region with a coherence gate as a boundary, and the mirror image is an image obtained by reversing the tomographic image of the adjacent region relative to the coherence gate.

10. The optical coherence tomography method according to claim 1, wherein when the measurement image is acquired, a position of a coherence gate is set on a side of an adjacent region to the measurement region with respect to a boundary between the measurement region and the adjacent region.

11. The optical coherence tomography method according to claim 1, wherein the object is a retina.

12. The optical coherence tomography method according to claim 1, wherein in the step of acquiring the tomographic image, the measurement image of a first measurement region is employed as the tomographic image of the first measurement region, and the tomographic image of a second measurement region is acquired by removing the mirror image of the tomographic image of the first measurement region from the measurement image of the second measurement region, wherein the first measurement region is the measurement region disposed at an end of the object, and wherein the second measurement region is the measurement region adjacent to the first measurement region.

13. An optical coherence tomography apparatus that divides light from a light source into measurement light and reference light and acquires a tomographic image of an object based on a wavelength spectrum of interfering light of the reference light and return light, the return light returning from the object upon irradiating the measurement light onto the object, the optical coherence tomography apparatus comprising:

a computer-implemented measurement image acquisition unit configured to acquire a measurement image based on the wavelength spectrum at each of a plurality of measurement regions of the object adjacent to one another in a direction of irradiation of the measurement light; and a computer-implemented tomographic image acquisition unit configured to acquire a tomographic image at each of the plurality of measurement regions by removing a mirror image of a tomographic image of an adjacent region being adjacent to the measurement region from the measurement image, wherein a computer used by the measurement image acquisition unit and by the tomographic image acquisition unit is included in the apparatus.

14. The optical coherence tomography apparatus according to claim 13, wherein the object is a retina.

15. The optical coherence tomography apparatus according to claim 13, wherein the tomographic image acquisition unit employs the measurement image of a first measurement region as the tomographic image of the first measurement region, and acquires the tomographic image of a second measurement region by removing the mirror image of the tomographic image of the first measurement region from the measurement image of the second measurement region, wherein the first measurement region is the measurement region disposed at an end of the object, and wherein the second measurement region is the measurement region adjacent to the first measurement region.

16. The optical coherence tomography apparatus according to claim 13, wherein the adjacent region is adjacent to the measurement region with a coherence gate as a boundary, and the mirror image is an image obtained by reversing the tomographic image of the adjacent region relative to the coherence gate.

17. An optical coherence tomography apparatus that acquires a tomographic image of an object based on interfering light resulting from interference between return light returning from the object upon irradiating measurement light onto the object and reference light corresponding to the measurement light, the optical coherence tomography apparatus comprising:

a computer-implemented acquisition unit configured to acquire a first measurement image based on an interfering light at a first measurement region of the object, and to acquire a second measurement image based on an interfering light at a second measurement region adjacent to the first measurement region in a direction of irradiation of the measurement light; and a computer-implemented removing unit configured to remove a mirror image of the first measurement image from the second measurement image, wherein a computer used by the acquisition unit and by the removing unit is included in the apparatus.

18. The optical coherence tomography apparatus according to claim 13, wherein when the measurement image is acquired, a position of a coherence gate is set on a side of an adjacent region to the measurement region with respect to a boundary between the measurement region and the adjacent region.

19. The optical coherence tomography apparatus according to claim 17, wherein the first measurement region is adjacent to the second measurement region with a coherence gate as a boundary, and the mirror image is an image obtained by reversing the first measurement image relative to the coherence gate.

20. The optical coherence tomography apparatus according to claim 17, wherein the tomographic image in the second measurement region is acquired by the removing unit.

21. The optical coherence tomography apparatus according to claim 17, further comprising a computer-implemented setting unit configured to set the first measurement region at an end of the object.

22. The optical coherence tomography apparatus according to claim 17, further comprising a computer-implemented changing unit configured to change a position of a coherence gate, wherein the first measurement image is acquired when the position of the coherence gate is at a first position, and the second measurement image is acquired when the position of the coherence gate is at a second position, which is different from the first position.

23. The optical coherence tomography apparatus according to claim 17, wherein the object is a retina.

24. The optical coherence tomography apparatus according to claim 17, wherein the first measurement region is the measurement region disposed at an end of the object, wherein the acquisition unit employs the first measurement image as the tomographic image of the first measurement region, and wherein the removing unit acquires the tomographic image of the second measurement region by removing the mirror image of the tomographic image of the first measurement region from the second measurement image.

25. The optical coherence tomography apparatus according to claim 17, wherein when the first measurement image is acquired, a position of a coherence gate is set on a side of the second measurement region adjacent to the first measurement region with respect to a boundary between the first measurement region and the second measurement region.

* * * * *